(12) United States Patent
Nettekoven et al.

(10) Patent No.: US 6,914,679 B2
(45) Date of Patent: Jul. 5, 2005

(54) SIDE LIGHT APPARATUS AND METHOD

(75) Inventors: Michael P. Nettekoven, Holden, MA (US); Darin Cerny, Hayward, CA (US)

(73) Assignee: Cognex Technology and Investment Corporation, Mt. View, CA (US)

( * ) Notice: Subject to any disclaimer, the term of this patent is extended or adjusted under 35 U.S.C. 154(b) by 471 days.

(21) Appl. No.: 10/024,898

(22) Filed: Dec. 18, 2001

(65) Prior Publication Data

US 2003/0112439 A1 Jun. 19, 2003

(51) Int. Cl.[7] ............................................... G01N 21/84
(52) U.S. Cl. ........................ 356/430; 356/431; 356/71
(58) Field of Search ........................ 356/429, 430–431, 356/237.1, 237.2, 237.3, 238.1, 238.2, 238.3, 71; 250/559.4, 223 R; 362/30, 323

(56) References Cited

U.S. PATENT DOCUMENTS

| | | | |
|---|---|---|---|
| 3,992,111 A | * | 11/1976 | Roulier et al. ............. 356/431 |
| 4,184,770 A | * | 1/1980 | Pinior ........................ 356/430 |
| 4,924,086 A | * | 5/1990 | Weber ........................ 250/235 |
| 4,969,037 A | | 11/1990 | Poleschinski et al. |
| 5,283,623 A | | 2/1994 | Muhlberg et al. |
| 5,940,149 A | | 8/1999 | Vanderwerf |
| 5,953,130 A | | 9/1999 | Benedict et al. |
| 5,978,090 A | | 11/1999 | Burri et al. |
| 6,025,905 A | | 2/2000 | Sussman |
| 6,170,973 B1 | | 1/2001 | Benedict |
| 6,191,850 B1 | | 2/2001 | Chiang |

FOREIGN PATENT DOCUMENTS

| | | |
|---|---|---|
| EP | 61217716 | 9/1986 |
| EP | 0400490 A2 | 5/1990 |
| EP | 02198128 | 8/1990 |
| EP | 03214974 | 9/1991 |
| EP | 09229632 | 9/1997 |
| EP | 11068197 | 3/1999 |

* cited by examiner

Primary Examiner—Gregory J. Toatley, Jr.
Assistant Examiner—Roy M. Punnoose
(74) Attorney, Agent, or Firm—Michael A. Jaskolski

(57) ABSTRACT

An apparatus for directing uniform intensity light onto a surface where the light is provided at an acute angle with respect to the surface including a light source that generates initial light rays that are essentially perpendicular to the surface and a guidance member positioned between the source and the surface which receives the initial rays and redirects the rays such that redirected rays are parallel and form acute angles with respect to the surface, the source and guidance member juxtaposed with respect to the surface so that the redirected rays subtend the surface.

13 Claims, 2 Drawing Sheets

SIDE LIGHT APPARATUS AND METHOD

STATEMENT REGARDING FEDERALLY SPONSORED RESEARCH

Not applicable.

CROSS-REFERENCE TO RELATED APPLICATIONS

Not applicable.

CROSS-REFERENCE TO RELATED APPLICATIONS

Not applicable.

BACKGROUND OF THE INVENTION

Machine vision devices are used in many manufacturing industries to identify either work piece defects or to identify known and expected patterns in work pieces. Generally, these vision systems include an illumination system or light source, a camera and a controller. The light source and camera are arranged adjacent a manufacturing line station. The source shines light on a surface of the work piece at the station and the camera is arranged such that a field of view (FOV) includes the illuminated surface of the work piece.

The controller is linked to the camera and causes the camera to periodically take exposures of the surface. The controller then compares each exposure or some characteristic thereof to ideal work piece characteristics (i.e., an ideal exposure or expected characteristic) and, based thereon, performs some function. Where unintended patterns or defects are identified, the controller may either flag the defective work piece for quality control purposes or, in the alternative, may log the unintended pattern or activate an indicator so that the overall manufacturing process can be adjusted thereby reducing the number of similar defects in the future.

One particularly useful area in which vision systems are used for both quality control and process adjustment purposes is in industries that manufacture planar web materials such as paper, metallic foils, etc., that are wound on rolls for delivery to end users. In web manufacturing applications, as in other vision system applications, a light source is used to illuminate a portion of the material and a camera is positioned to obtain exposures of at least a segment of the illuminated portion. However, because of the nature of the materials being examined and how the materials are typically stored, vision systems used with web based applications have additional requirements.

First, as a material web is being moved about a facility and prior to winding on a roller or roller, the web typically vibrates such that obtaining any type of meaningful image of the web material is difficult at best. Similarly, during transport, web material characteristics change as a function of system parameter settings and operation. For instance, the tension between adjacent web transport rolls tends to stretch the web to varying degrees during transport. For this reason, even if vibrations were minimal at some point during the manufacturing process, images at most points along web transport would vary as a function of system parameters such that the images would be imperfect for determining the characteristics of the end product.

For these reasons, in the case of imaging web products, vision systems typically are used to examine the end web product as the product wraps about a roller just prior to the web being wound on an end spool. By inspecting the web on the roller adjacent an end spool, the inspection point is rendered relatively stable and therefore vibrations are minimized.

In addition, examining the web on a roller instead of on the end spool avoids problems with attributing sensed defects to wound web sections. For instance, assume a small but persistent defect occurs along the length of a web material being wound on an end spool and that the material is being examined as it accumulates on the end spool. In this case, during a first winding, the degree of defect reflects reality and is relatively minimal. However, during a second winding, assuming the defect remains aligned at the same point along the web width, the defects from the first two windings accumulate and the defect sensed during the second winding appears greater than it is in reality. This cumulative process continues and the sensed degree of defect continues to grow. Complicating matters further, once defects have accumulated there is no way to attribute portions of the cumulative defect to web segments.

Second, a camera set and light source having a special field of view is typically used to examine roller supported web material. To this end, the term "cross direction" or first direction will be used hereinafter to refer to the dimension of a web supported material along the length of the roller (i.e., along the width of a web). In order to simplify this explanation the direction along a web surface perpendicular to the cross direction and tangent to the radius of curvature of an outwardly facing segment of the web at a given point will be referred to as "machine direction" or second direction. In order to get consistent inspection over 100% of the product surface, image data is collected along a line parallel to the roller cross direction (i.e., the roller length dimension).

For this reason, in order to reduce the variance among exposures as material is inspected, in web-roller based applications, the light source is typically designed to concentrate a bright light into a narrow line along a cross direction (i.e., width) segment of the material and a camera is designed and positioned to have a linear field of view that collects image data from the illuminated segment. The camera can be oriented to view a direct reflection of the illuminated segment (i.e., be placed directly in the path of reflected light rays) or direct transmission of the illuminated segment (i.e. be placed on a side of the web opposite the light so light transmitted through the web is detected by the camera). Images generated with a camera that views a direct reflection or direct transmission are generally referred to as "bright field" images. In the alternative, the camera can be oriented "off-axis" relative to the reflected or transmitted light rays resulting in a so-called "dark field" image.

Third, in most cases web type material defects are topographical along the surface of the material including bumps, indentations, etc. Such defects can be illuminated best where light is directed at an angle with respect to the surface of the web so that the defects cause shadows across the web material surface.

One way to provide light at an angle with respect to the web material surface is to provide a line source adjacent the outward facing web material surface and direct light rays at an angle with respect to the machine direction. While this solution facilitates observation of web defects along the material direction, unfortunately, this solution fails to facilitate observation of cross direction defects along the web width. Web generating processes typically vary more across web width than along web length and therefore, while this solution may enable identification of some web material defects, many defects are unobservable in this manner.

One way to provide light at an angle with respect to the cross direction dimension of a material web has been to provide a bright side light on the side of a roller (i.e., at a roller end) that shines light along rays that form a small "incidence angle" with the web cross direction dimension. While this solution works well at points near the side light source, unfortunately, along the web material width, light intensity tapers off and therefore imaging results along the cross direction are inconsistent. In addition, in the case of side light illumination, the incident angle of a light and the outward facing web material surface may vary over the entire inspected surface. Variables such as differing light intensity along web material width and changing incident angles complicate vision system tasks and therefore should be avoided whenever possible.

Therefore, a need exists for an illumination system that can provide even intensity light at a uniform angle with respect to the cross direction of a web or planar material for imaging purposes so that defects across the cross direction can be highlighted and identified.

SUMMARY OF THE INVENTION

It has been recognized that an ideal light source for illuminating surface defects in a flat surface material must generate light having three characteristics. First, the light rays should be parallel to each other so that defects create relatively dark shadows. Second, the rays that subtend the flat surface should have essentially identical intensity at the subtended surface so that light variance at the surface is completely a function of surface topology and not of light source anomalies. Third, the rays should be angled so as to have a component that forms an angle with the surface so that defects block rays and create identifiable shadows. In addition, in the case of a web supported material web, to illuminate defects along the web width (i.e., along the cross direction dimension), the rays should be angled so as to have a lateral component aligned with the web cross direction dimension.

To provide a light source having all of the desirable characteristics described above, an exemplary embodiment of the invention includes a uniform light source and a guidance member where the light source generates parallel uniform light rays that are essentially perpendicular to at least one flat dimension of a surface to be illuminated. The guidance member is constructed so as to receive parallel light rays and alter the paths of the received rays so that redirected rays emanating from the member are parallel and angled with respect to the received rays. The guidance member is positioned generally between the source and the surface to be illuminated and such that the rays emanating from the guidance member are angled and have a component along the flat dimension of the surface to be illuminated. In the case of a roller supported web material, the flat dimension is along the web width (i.e., the cross direction) and therefore the redirected rays have a lateral component aligned with the web width as desired.

Positioning the uniform source parallel to the surface to be illuminated ensures uniform illumination of the surface. When so positioned, the distances traveled by light rays from the source to the surface are identical and thus intensity should be identical.

Thus, the present invention provides a simple and inexpensive light source that has ideal characteristics for illuminating flat surfaces including but not limited to roller supported web materials.

Consistent with the objects and advantages described above, the invention includes an apparatus to be used to illuminate an object having an essentially flat surface along a first dimension that extends along a first direction, the apparatus for providing light that is directed onto the flat surface in a direction that has at least some component in the first direction. The apparatus comprises a light source that forms a plurality of initial light rays that are directable along a direction essentially perpendicular to the first direction and a guidance member positioned proximate the light source that intercepts and redirects the initial light rays such that redirected rays exit the guidance member along paths that form angles with the respect to the initial rays and which have a lateral component aligned with the first direction and so that the redirected rays subtend a field of illumination of the flat surface.

The light source may be positioned such that the initial rays are essentially perpendicular to the flat surface and the guidance member preferably redirects the rays such that the redirected rays are essentially parallel to each other. The light source may be a line light source having a line surface from which light emanates, the source positionable such that the line surface is parallel to the flat surface and extends in the first direction.

The invention may also be for collecting images of the illuminated portion of the flat surface and further, in this case, includes a camera having a field of view and positionable such that the field of view includes at least a segment of the field of illumination on the flat surface.

The flat surface may have a second dimension perpendicular to the first dimension and the source may be positioned such that the initial rays are angled so as to have a longitudinal component aligned with the second direction.

The object may be a sheet of material supported over a roller, a sheet of material on an "open run" (i.e., material between two supporting rollers—this, provided that the examined segment of material is held stable in some fashion) or a sheet of material wrapped around a spindle such that the first dimension is along the width of the material and a second dimension is perpendicular to the first dimension and, wherein, the source is positionable essentially parallel to the first dimension. Here, the light source may have a length dimension along its length that is essentially identical to the first dimension and the light source and guidance member may be offsetable with respect to the flat surface along the first direction such that the redirected rays subtend the flat surface along essentially the entire first dimension. Also, in this case, the initial rays may have a longitudinal component in the second direction.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DESCRIPTION OF THE PREFERRED EMBODIMENT

Figure 1:
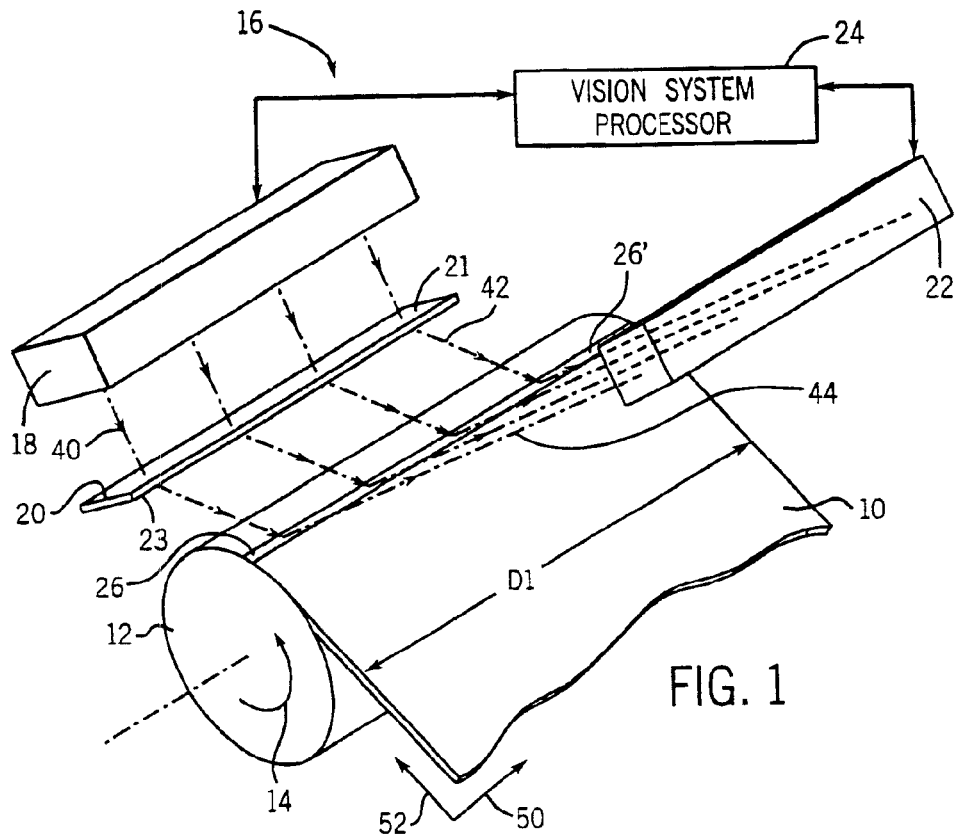
FIG. 1 is a perspective view of the inventive light source in the context of a roller supported web sheet imaging system.

Referring now to FIG. 1, the present invention will be described in the context of an exemplary vision system 16 for identifying defects in a web material. To this end, as illustrated, a web material or sheet 10 is being fed to and is running over roller 12 from another roller (not illustrated) with roller 12 rotating in a direction indicated by arrow 14. Web sheet 10 and roller 12 each have a width dimension D1. Consistent with terminology used in the art, sheet 10 is moving in a "machine" direction identified by arrow 52 as sheet 10 is passing over roller 12 and the direction perpendicular to the machine direction and parallel to dimension D1 is referred to herein generally as a "cross direction" identified by numeral 50.

Referring still to FIG. 1, the image generating system 16 includes a light source 18, a guidance member 20, a camera 22 and a vision system processor 24. Processor 24 is linked to each of light source 18 and camera 22 and controls operation thereof. For instance, system processor 24 provides power to light source 18 to turn light source 18 on and off. With respect to camera 22, processor 24 provides activation signals to camera 22 thereby causing camera 22 to acquire imaging data corresponding to whatever is within the camera's field of view. In addition, when camera 22 acquires imaging data, system processor 24 may receive and process that data or store the data for post-acquisition processing purposes.

In the illustrated embodiment camera 22 generally includes one or more line cameras having a total length FOV dimension L1 that is essentially identical to the web width dimension D1 such that the total length FOV is capable of acquiring data corresponding to the entire width D1 of web sheet 10.

Figure 2:
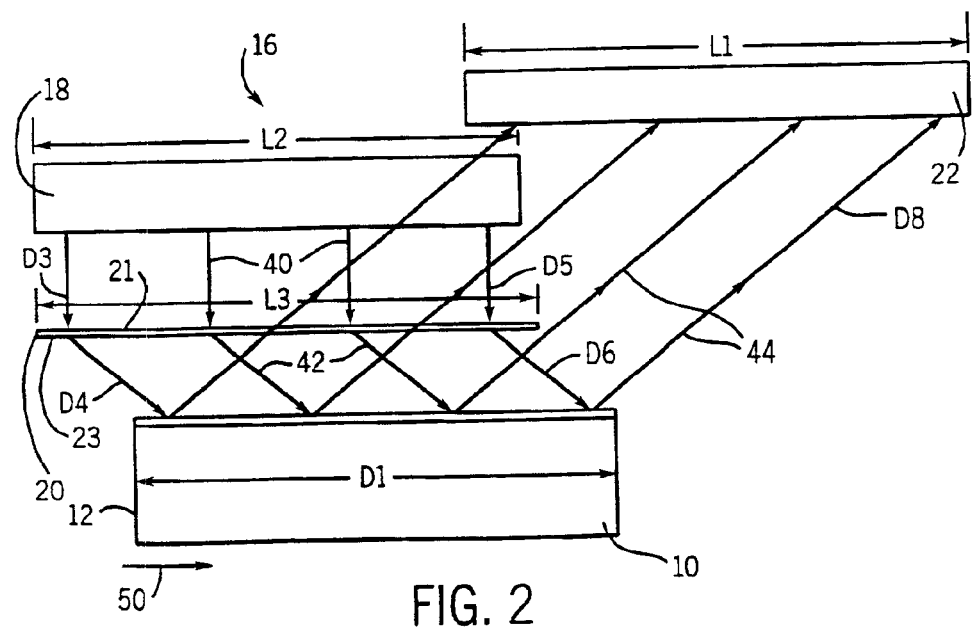
FIG. 2 is a plan front view of the image of FIG. 1.

Referring still to FIG. 1 and also to FIG. 2, light source 18 is a uniform line light source meaning that the light source generates parallel light rays (e.g., 40) that emanate from a line along a light source length L2. Light source length L2 is essentially identical to camera length L1 and sheet width D1 so that source 18 is capable of illuminating a segment 26' of web sheet 10 across the entire width dimension D1.

Figure 3:
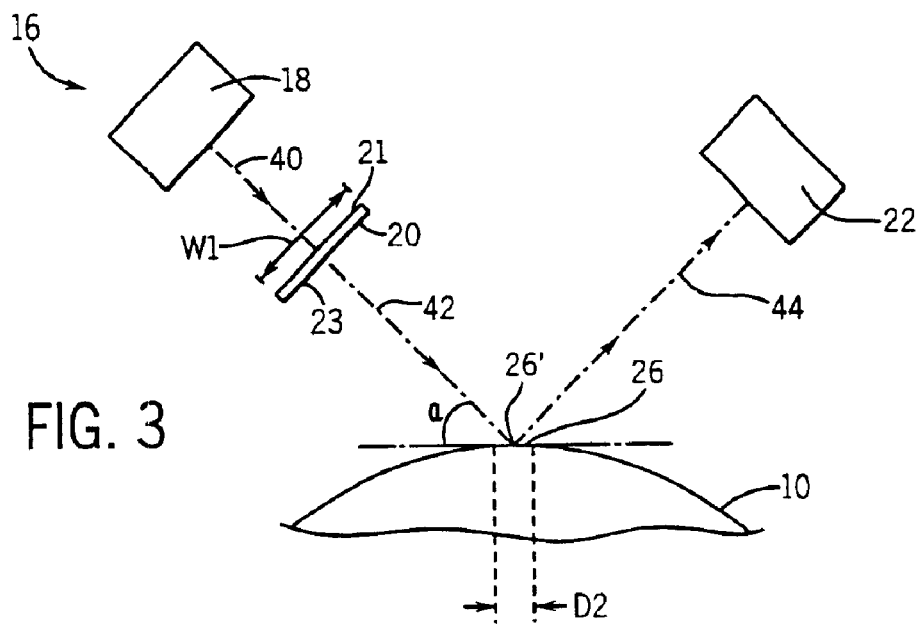
FIG. 3 is a partial side plan view of the system of FIG. 1.

Referring still to FIGS. 1 and 2, guidance member 20 is an elongated member having a length L3 which is essentially identical or perhaps slightly longer than light source length L2 and having a width W1 (see also FIG. 3) sufficient to ensure that all light emanating from the light source 18 subtends the member 20. Member 20 is constructed such that the member receives light rays at a first surface 21 and redirects the light rays such that rays emanating form a second surface 23 opposite the first surface 21 are redirected. More specifically, when a light ray is perpendicular to and subtends first surface 21, member 20 redirects the ray such that a ray emanating from surface 23 forms an acute angle γ with respect to second surface 23 along a path having a lateral component that is aligned with length dimension L3. Referring also to FIG. 3, in the present example, guidance member 20 does not modify ray direction along width dimension W1 and therefore, as illustrated, a ray which is perpendicular to surface 21 when it enters guidance member 20 is also perpendicular with width W1 when it exits member 20. Member 20 in at least one embodiment can be formed using a prismatic film like the films sold by 3M that are formed of transparent acrylic or polycarbonate polymer in sheet forms of approximately 20 mils thickness.

Figure 5:
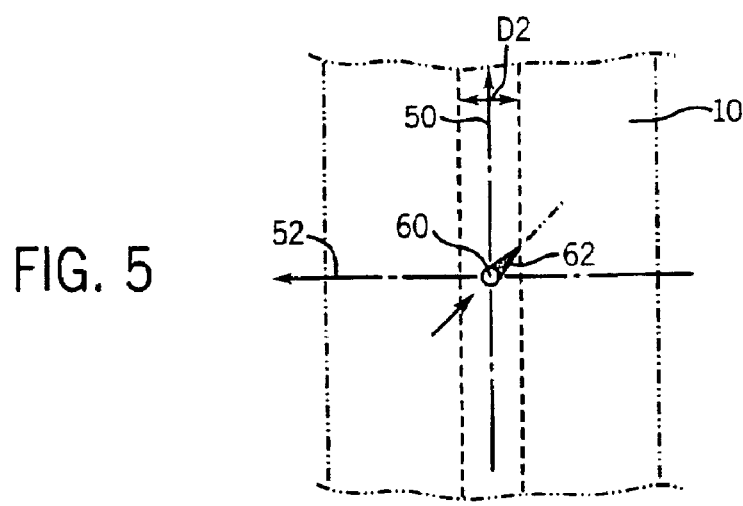
FIG. 5 is a top plan view of the schematic illustrated in FIG. 4.

Referring to FIGS. 1 through 3, source 18 is generally used to illuminate a field of illumination (FOI) 26 through which web sheet 10 is transported. Because source 18 is a line light source having a very narrow width (not separately labeled) and a length dimension L2 (see FIG. 2), FOI 26 is characterized by similar dimensions. Thus, in FIG. 1, FOI 26 has a length dimension identical to web sheet width D1 and, as best seen in FIGS. 3 and 5, FOI 26 has a width dimension D2 that is relatively narrow. It should be appreciated that, despite the fact that dimension D2 may occur on the outward facing surface of a roller supported web sheet 10 and therefore there would be some curvature along dimension D2, where dimension D2 is extremely narrow the radius of curvature is so large that, for all practical purposes, the surface of a sheet segment in FOI 26 may be considered essentially flat along D2 dimension. Consistent with the description above, long dimension D1 of FOI 26 will also be referred to as a cross-direction dimension and small dimension D2 will also be referred to as a machine direction dimension.

Referring still to FIGS. 1, 2 and 3, in general, light source 18 generates initial light rays 40 which are directed toward member 20 and redirected rays 42 emanating from member 20 are directed at web sheet 10 thereby illuminating a segment 26' of sheet 10 within FOI 26. Rays 42 subtending segment 26' are reflected and the reflected rays 44 are detected by camera 22 (e.g., the set of cameras that comprise camera 22). More specifically, in the illustrated embodiment, light source 18 is juxtaposed with respect to roller 12 such that the initial light rays 40 are essentially perpendicular to cross-direction dimension D1 of segment 26' and form an acute angle α (best seen in FIG. 3) with machine direction dimension D2. In addition, source 18 is offset along the cross direction some amount from sheet 10 (see FIG. 2). The amount of offset required is a function of the distance from the sheet to guidance member 20 and the angle at which member 20 redirects the light.

Guidance member 20 is generally positioned between light source 18 and segment 26 such that the length L3 of member 20 is aligned with light source length L2 and member 20 is generally parallel with source 18 and segment 26'. When so positioned, initial light rays 40 from opposite ends of source 18 travel identical distances D3 and D5 prior to subtending surface 21 of member 20. Similarly, other light source rays travel distances identical to distance D3 prior to subtending surface 21.

Guidance member 20, as described above, redirects the received rays 40 so that redirected rays 42 are directed toward and illuminate segment 26'. Thus, redirected rays 42 are each angled with respect to initial rays 40 such that redirected rays 42 have a lateral component that is aligned with cross-direction 50 and hence with web width D1. Importantly, because member 20 and illuminated segment 26 are essentially parallel, the distances traveled by all redirected rays 42 between member 20 and segment 26' are essentially identical. For instance, the distances D4 and D6 corresponding to redirected rays 42 associated with opposite ends of light source 18 are essentially identical.

It should be appreciated that because the distances (e.g., D3) traveled by each ray 40 between source 18 and member 20 are identical and the distances (e.g., D4) traveled by each ray 42 between member 20 and segment 26' are identical, the combined distances (e.g., D3+D4; D5+D6, etc.) traveled by each ray between source 18 and segment 26' are identical and therefore the intensity of all rays that illuminate segment 26' should be identical.

Redirected rays 42 that subtend segment 26' are reflected and the reflected rays 44 are detected by camera 22. In the illustrated embodiment, camera 22 is positioned parallel to segment 26'.

Figure 4:
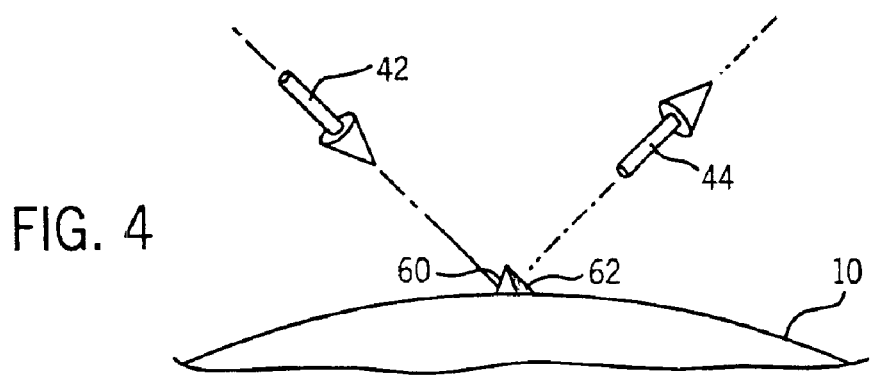
FIG. 4 is a schematic diagram illustrating light generated by the inventive light source and a material defect illuminated thereby.

Referring still to FIGS. 1 through 3 and also to FIGS. 4 and 5, it should be appreciated that the light rays 42 that subtend segment 26' within FOI 26 have ideal illuminating imaging properties. To this end, first, because source 18 is uniform (i.e., all rays have identical intensities) and the distances traveled by each ray from source 18 to segment 26' are identical, the rays 42 subtending segment 26' have identical intensities. Second, referring specifically to FIG. 3, because source 18 is positioned so that rays 40 form an acute angle with respect to FOI 26 dimension D2, any web sheet defects along machine direction dimension D2 should cast a shadow that can be detected. Third, light from guidance member 20 is angled with respect to cross-direction dimension D1 of segment 26' and therefore any defects along cross-direction dimension D2 should cast a shadow that can be detected.

Referring now to FIGS. 4 and 5, an exemplary defect in the form of a bump 60 on a web sheet 10 is illustrated along with a shadow 62 that is generated by the inventive light source 18 illustrated in FIGS. 1 through 3. The cross-direction 50 and machine direction 52 are indicated in FIG. 5. Consistent with the system of FIGS. 1 through 3, redirected light rays 42 that emanate from member 20 are angled so that they have a lateral component aligned with cross-direction 50 (i.e., a cross-direction component) and a longitudinal component aligned with machine direction 52. Referring also to FIG. 1, as roller 12 is rotated in direction 14 to pass sheet 10 thereon, when segment 26' of sheet 10 including defect 60 comes within FOI 26, redirected rays 42 subtend the defect 60, defect 60 blocks some of the rays 42 and the shadow 62 results. Camera 22 acquires image data corresponding to FOI 26 and therefore collects data useable to identify the existence of shadow 62 and hence the existence of defect 60. Processor 24, identifying defect 60 and perhaps other defects, may perform any of several different functions.

It should be understood that the methods and apparatuses described above are only exemplary and do not limit the scope of the invention, and that various modifications could be made by those skilled in the art that would fall under the scope of the invention. For example, while the invention is described as one wherein source 20 is positioned so that initial rays 40 form an acute angle α with respect to dimension D2 (see FIG. 3), the invention also contemplates configurations where initial rays 40 are perpendicular to dimension D2 or, indeed, where camera 22 and source 20 are on the same side of a plane that is perpendicular to dimension D2. In addition, while camera 22 is shown within the path of reflected rays 44 (i.e., a "bright field" position), some embodiments will include an off axis camera (i.e., a "dark field" position). Moreover, while advantageous for use with roller supported web materials, the invention is also useful in other applications such as illuminating planar sheet materials and surfaces to illuminate defects and may also be used to illuminate a web as the web accumulates on a spindle. In these cases, while illustrated source 18 is line source, in some embodiments source 18 may be a sheet light source with a similarly configured guidance member 20.

To apprise the public of the scope of this invention, the following claims are made:

What is claimed is:

1. An apparatus to be used to illuminate an object having an essentially flat surface along a first dimension that extends along a first direction, the apparatus for providing light that is directed onto the flat surface in a direction that has at least some component in the first direction, the apparatus comprising:
    a light source that forms a plurality of initial light rays that are directable along a direction essentially perpendicular to the first direction; and
    a guidance member positioned proximate the light source that intercepts and redirects the initial light rays such that redirected rays exit the guidance member along paths that form angles with respect to the initial rays and which have a lateral component aligned with the first direction and so that the redirected rays subtend an illuminated portion of the flat surface.

2. The apparatus of claim 1 wherein the light source is positioned such that the initial rays are essentially perpendicular to the flat surface.

3. The apparatus of claim 1 wherein the guidance member redirects the rays such that the redirected rays are essentially parallel to each other.

4. The apparatus of claim 1 wherein the light source is a line light source having a line surface from which light emanates, the source positioned such that the line surface is parallel to the flat surface and extends in the first direction.

5. The apparatus of claim 1 also for collecting images of the illuminated portion of the flat surface and further including a camera having a field of view and positioned such that the field of view includes at least a segment of the illuminated portion of the flat surface.

6. The apparatus of claim 1 wherein the flat surface has a second dimension perpendicular to the first dimension and wherein the source is positioned such that the initial rays are angled so as to have a longitudinal component aligned with the second direction.

7. The apparatus of claim 1 wherein the guidance member is a prismatic film.

8. The apparatus of claim 7 wherein the source is a line source having a line surface from which light emanates, the source positioned such that the line surface is essentially parallel to the flat surface of the object and extends in the first direction.

9. The apparatus of claim 8 wherein the object is a sheet of material wrapped around a role such that the first dimension is along the width of the roll and a second dimension is perpendicular to the first dimension and, wherein, the source is positioned essentially parallel to the first dimension.

10. The apparatus of claim 9 wherein the light source has a length dimension along its length that is essentially identical to the first dimension and wherein the light source and guidance member are offsetable with respect to the flat surface along the first direction such that the redirected rays subtend the flat surface along essentially the entire first dimension.

11. The apparatus of claim 9 wherein the initial rays have a longitudinal component in the second direction.

12. The apparatus of claim 11 also for collecting images of the illuminated portion of the flat surface and further including a camera having a field of view and positioned such that the field of view includes at least a segment of the illuminated portion of the flat surface.

13. The apparatus of claim 1 wherein the guidance member is positioned at least in part between the source and the flat surface.

* * * * *